United States Patent [19]
Charlton et al.

[11] Patent Number: 6,096,269
[45] Date of Patent: Aug. 1, 2000

[54] ANALYTE DETECTION DEVICE AND PROCESS

[76] Inventors: Steven C. Charlton, 12075 Douglas Rd., Osceola, Ind. 46561; Michael J. Wilcox, 225 Myrtle St., Elkhart, Ind. 46514

[21] Appl. No.: 08/102,297

[22] Filed: Aug. 5, 1993

[51] Int. Cl.[7] .................................................. G01N 33/48
[52] U.S. Cl. ................................. 422/58; 422/61; 436/95
[58] Field of Search .................................. 422/56–58, 61; 436/95, 63

[56] References Cited

U.S. PATENT DOCUMENTS

| | | | |
|---|---|---|---|
| 4,776,904 | 10/1988 | Charlton et al. | 422/56 |
| 5,037,738 | 8/1991 | Lamos et al. | 436/95 |
| 5,087,556 | 2/1992 | Ertinghausen | 422/58 |
| 5,213,966 | 5/1993 | Vuorinen et al. | 436/95 |

*Primary Examiner*—Lyle A. Alexander
*Attorney, Agent, or Firm*—Jerome L. Jeffers

[57] ABSTRACT

The present invention provides a device and a process for detecting an analyte in a biological fluid. That device comprises a cover portion with a restricted area for sample application, a separation matrix for separation of the analyte from substances in the sample that can interfere with detection of the analyte and means for detecting the analyte. The restricted area of sample application is less than 90 percent of the cross-sectional area of the separation matrix and the separation matrix and the means for detecting analyte are under compression of between 14 to 43 percent. A process comprises applying a sample of fluid to such a device and detecting a signal generated from an interaction between the analyte and the detection means in the device.

32 Claims, 2 Drawing Sheets

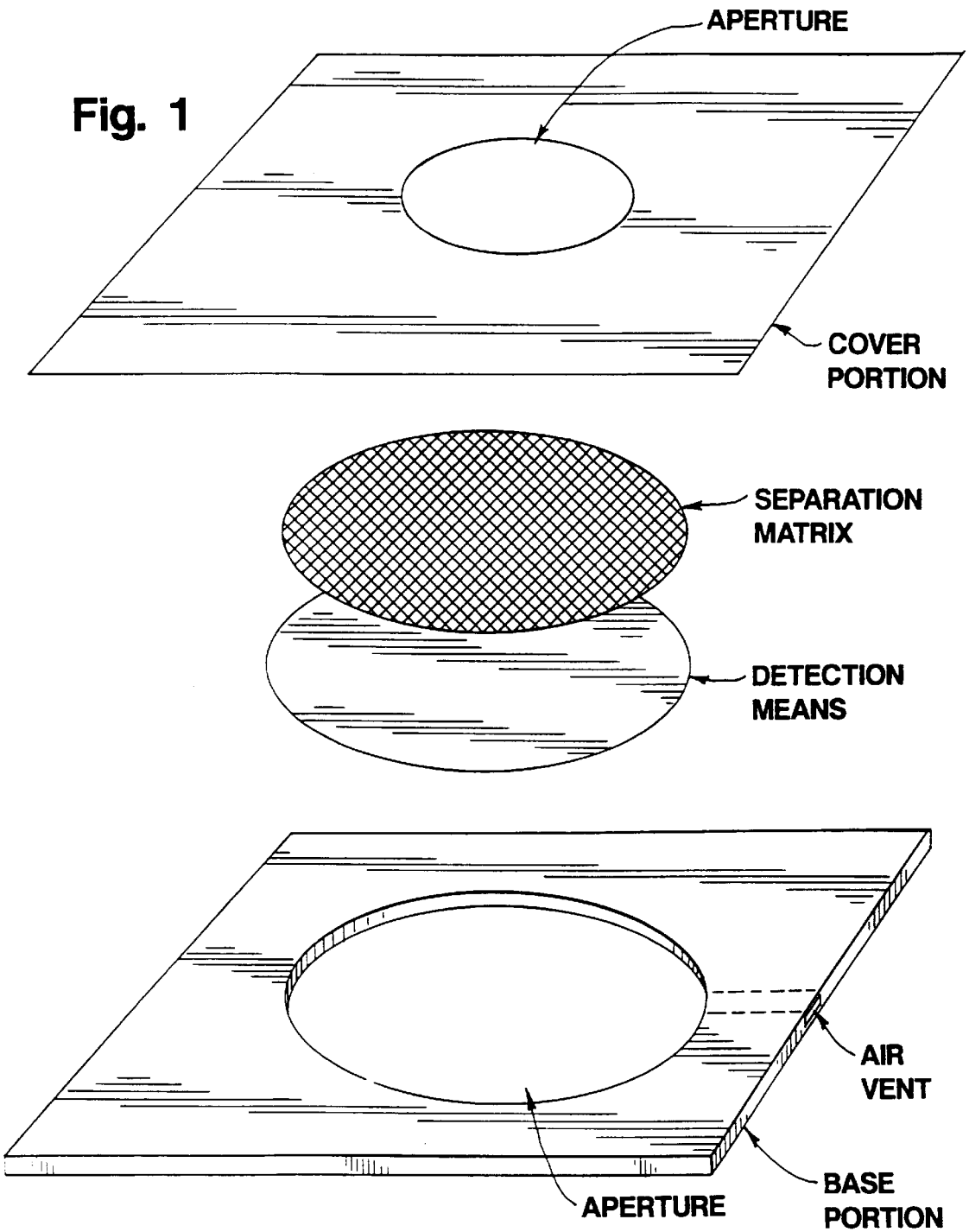

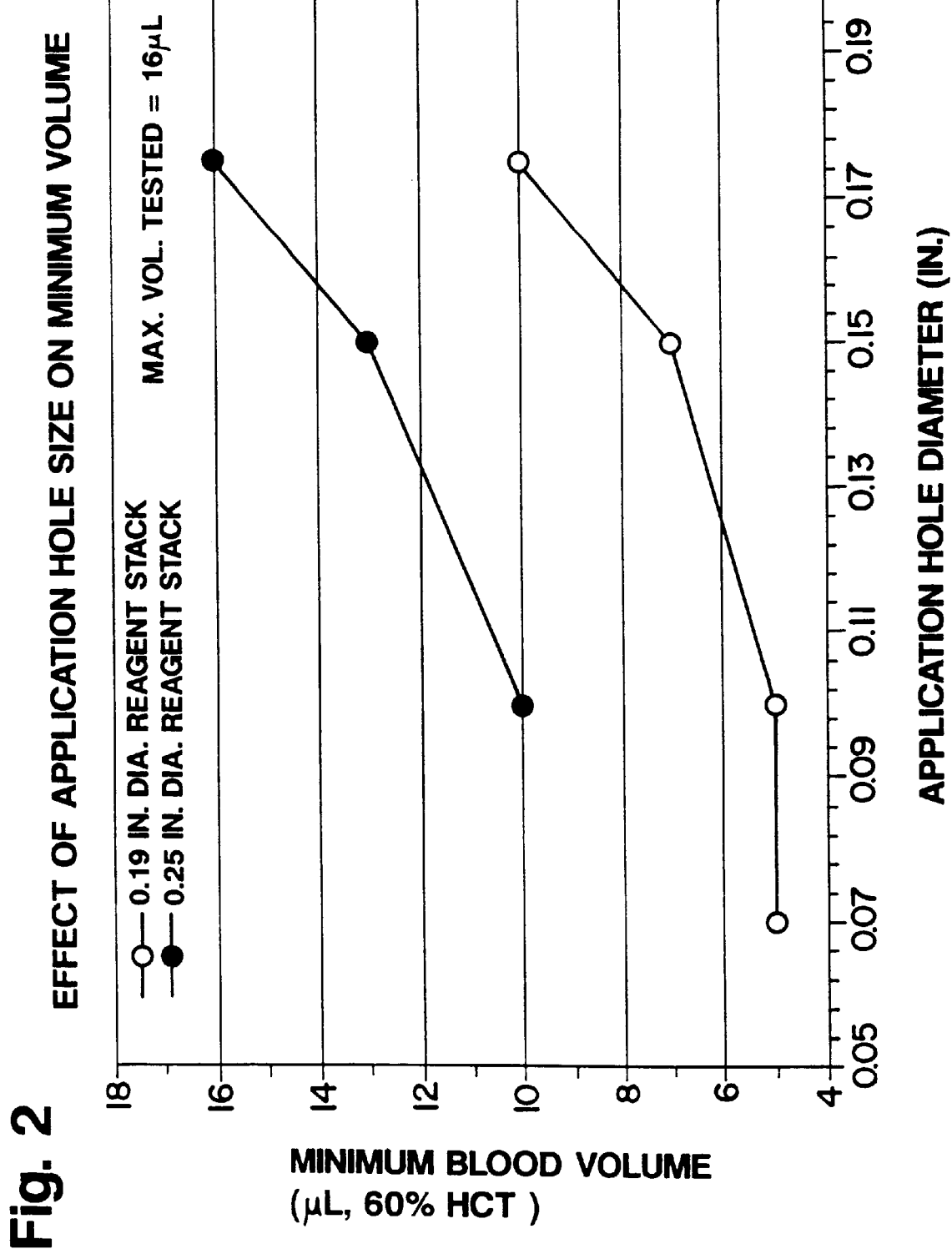

ANALYTE DETECTION DEVICE AND PROCESS

BACKGROUND OF THE INVENTION

A. Technical Field of the Invention

The present invention relates to a device and a process for detecting an analyte in a biological fluid. That device comprises a cover portion with a restricted area for sample application, a separation matrix for separation of the analyte from substances in the sample that interfere with detection of the analyte, means for detecting the analyte and a base portion having a window or opening for measuring the analyte. A process comprises applying a sample of fluid to such a device and detecting a signal generated from an interaction between the analyte and the detection means in the device.

B. Description of the Background Art

There is a need in the analyte detection art for devices and methods that allow for the rapid, accurate determination of biological fluid analyte composition in very small sample sizes. The need for a device using small sample volumes is particularly relevant to the detection of blood analyte composition because of the difficulty and inconvenience of obtaining blood samples from subjects.

Currently available such devices include ACCUCHEK EASY TEST STRIPS™ and ACCUTREND® (Boehringer Mannheim Corp.). Those devices are multilayer reagent systems characterized by non-restricted application-site sizes.

The present invention provides a detection device having a limited application area compared to an underlying separation matrix, which serves to reduce the volume of fluid and time needed for analyte detection. In addition, the separation matrix and underlying detection means are maintained under a required compression state of 14 to 43 percent, based on an uncompressed relaxed state. Preferably, the compression is between 20 and 35 percent that of a relaxed (uncompressed) state.

SUMMARY OF THE INVENTION

In one aspect, the present invention contemplates a device for assaying an analyte in a biological fluid, which device comprises:

a) a base portion having a transparent window or opening;

b) means for detecting an analyte vertically adjacent to and at least partially coincident with that window or opening;

c) a separation matrix vertically adjacent to and substantially coincident with the detection means such that the analyte can move from the separation matrix to the detection means; and d) a cover portion having an aperture, the cross-sectional area of which aperture is less than about 90 percent of the cross-sectional area of the separation matrix and preferably, less than about 50% of the cross-sectional area of the separation matrix. The separation matrix and the detection means are maintained in a compression state of 14 to 43 percent, based on a relaxed state, and preferably, under a compression of 20 to 35 percent.

Preferably, a transparent window is present in the base portion and is made glass or plastic such as polycarbonate. The detection means is preferably a matrix containing chemical reagents for detecting the analyte.

In a preferred embodiment, the liquid sample is a sample of extracellular fluid as exemplified by whole blood. A preferred analyte that is detected by a device of the present invention is glucose, cholesterol, amylase or triglycerides. Where the analyte is glucose, a preferred detection means is a membrane containing means for detecting glucose, which means preferably comprise ATP, NAD, hexokinase, glucose-6-phosphate dehydrogenase, diaphorase and an indicator.

In a preferred embodiment, a separation matrix is a membrane filter and preferably a glass fiber filter. More preferably, the glass fiber filter has a sample application side adjacent to the cover portion and a reagent side adjacent to the detection means, whereby the glass fibers at the reagent side are shorter than the glass fibers at the application side.

The separation matrix can contain an aggregation-promoting substance that promotes aggregation of colloidal particles or cells or a surface active agent such as a non-hemolytic surfactant. In another preferred embodiment, a separation matrix contains HEPES buffer.

In another aspect, the present invention contemplates a device for assaying blood glucose comprising:

a) a plastic base portion having a polycarbonate clear window;

b) a synthetic membrane vertically adjacent to the base portion and at least partially coincident with the window, which synthetic membrane contains ATP, NAD, hexokinase, glucose-6-phosphate dehydrogenase, diaphorase and an indicator;

c) a glass fiber filter vertically adjacent to the reagent membrane and substantially coincident with that reagent membrane; and d) a thermoformed polystyrene cover portion having an aperture, the cross-sectional area of which aperture is less than about ninety percent of the cross-sectional area of the glass fiber filter and, more preferably, less than about fifty percent of the cross-sectional area of the glass fiber filter.

BRIEF DESCRIPTION OF THE DRAWINGS

In the drawings which form a portion of the specification:

FIG. 1 shows a schematic representation of a detection device.

FIG. 2 shows the effects of application-site size on the detection of analyte.

DETAILED DESCRIPTION OF THE PREFERRED EMBODIMENTS

I. Analyte Detection Device

A device of the present invention is a multilayer reagent system device for detection of an analyte in a liquid sample. Such a device comprises two layers situated vertically adjacent to one another (e.g., one layer is above the other).

A first layer serves at least to receive the liquid sample containing the analyte to be detected and to separate that analyte from other substances in the sample that interfere with detection of the analyte. As used herein, the phrase "separation matrix" means a layer that receives the sample and performs the separating function.

A second layer receives the analyte from the separation matrix and serves at least to detect the analyte. As used herein, the word "detect" or its grammatical equivalents means measuring the analyte and generating a detectable signal indicative of analyte presence or preferably proportional to the amount or concentration of that analyte. As used herein, the phrase "detection means" refers to a layer that serves that detection function.

Typically, a separation and a detection means are sandwiched between additional layers that serve to support and compress the separation and detection means, allow access to the separation matrix for sample application and permit detection of a generated signal.

Thus, in one aspect, the present invention contemplates a device for detecting an analyte in a liquid sample, which device comprises:

a) a base portion having a transparent window or opening;

b) means for detecting the analyte vertically adjacent to the base portion and at least partially coincident with that window or opening;

c) a separation matrix vertically adjacent to and substantially coincident with that detection means such that the analyte can move from the separation matrix to the detection means; and d) a cover portion having an aperture, the cross-sectional area of which aperture is less than the cross-sectional area of the separation matrix.

A base portion of a device of the present invention can be fabricated of any material that is (1) chemically-resistant to a sample being analyzed (including the analyte and constituents of that sample) and to other reagents used in the device (e.g., means for detecting an analyte) and (2) nonreactive (i.e., chemically-inert) with respect to other components of the device.

Exemplary chemically-resistant and inert materials include glass, plastic and metal. A preferred material is a plastic such as polystyrene. Means for fabricating materials into a base portion of suitable shape and size are well known in the art.

A base portion contains an aperture (window) that provides access to a detection matrix. Such access is needed for visualization or otherwise detection of a signal generated from an interaction between an analyte and a means for detecting that analyte.

In a preferred embodiment, an aperture in a base portion is covered with a transparent material that permits visualization of a generated signal. A transparent material used as a cover is fabricated of a chemically-resistant and chemically-inert substance as set forth above. A preferred transparent material is a transparent plastic such as polycarbonate.

A device of the present invention has a detection means vertically adjacent to a base portion. At least a portion of the detection means is aligned coincident to an aperture in the base portion to allow for visualization of the detection means through the base portion. In a preferred embodiment, means for detecting an analyte is a detection matrix. As used herein, the term "matrix" indicates a substance that encloses, contains or embeds another substance.

A detection matrix used in a device of the present invention encloses, contains or embeds means for detecting an analyte. A detection matrix is preferably a membrane fabricated of natural or synthetic material. Such membrane material is chemically-resistant and chemically-inert as those terms are defined above. Preferably, a detection membrane is fabricated of synthetic material such as those set forth below in Table 1.

TABLE 1

| Source | Trade Name | Type | Membrane Charge | Pore Sizes (microns) |
| --- | --- | --- | --- | --- |
| PALL | Biodyne A | Nylon | Zwitterion | 0.2, 0.45, 0.65, 1.2 and 3.0 |
| | Biodyne B | Nylon | positive charged | 0.2, 0.45, 1.2 and 3.0 |
| | Biodyne C | Nylon | negative charged | 0.2, 0.45, 1.2 and 3.0 |
| | Loprodyne | Nylon | noncharged | 0.2, 0.45, 1.2 and 3.0 |
| S & S | Nylon 66 | Nylon | noncharged | 0.45 and 0.65 |
| | Nytran | Nylon | positive charged | 0.45 and 0.65 |
| | Optibind | Nitrocellulose | noncharged | 0.45 |
| | Plastic Backing | Nitrocellulose | noncharged | 0.45 |
| CUNO | Zeta Bind | Nylon | noncharged | 0.45 and 0.65 |
| | Zeta Bind | Nylon | positive charged | 0.45 |
| MSI | Magnagraph | Nylon | positive | 0.45 and 0.65 |
| | Magna | Nylon | noncharged | 0.45 and 0.65 |
| MILLIPORE | Duropore | Polyvinyl-idene Fluoride | noncharged | 0.65 |
| GELMAN | Versapor | Acrylic copolymer | noncharged | 0.2 and 0.45 |
| | AP450 | Acrylic copoiymer | noncharged | 0.45 |
| | Thermapor | Poly-sulfone | noncharged | 0.8 |
| | Ultrabind | Affinity Binding | noncharged | 0.45 |
| MEMTEC | Filterite | Poly-sulfone | asymmetric pore | 0.2 |
| | Memtest | Affinity Binding | noncharged | 0.8 |

A detection matrix is preferably of low porosity. Preferred pore sizes are from about 0.2 microns to about 3.0 microns and, more preferably from about 0.45 to about 0.65 microns. A low porosity prevents movement of the sample out of the detection matrix and restricts the flow of red blood cells. It also provides opacity.

Those chemical reagents interact with an analyte so as to generate a physical or chemical signal that is indicative of analyte presence. Preferably, a signal generated is proportional to the amount or concentration of analyte in the detection matrix and sample. Chemical reagent means for detecting an analyte are well known in the art. By way of example are colorimetric systems for detection of analytes such as protons (pH), phosphate, creatinine, glucose, cholesterol, amylase, triglyceride, protein, sulfate and the like.

In a preferred embodiment, means for detecting an analyte comprises one or more chemical reagents for a calorimetric assay of that analyte. In one embodiment, the analyte is glucose and the means for detecting glucose comprise chemical reagents needed to detect glucose in accordance with the well known hexokinase reaction. The chemical reactions involved in that reaction are set forth below.

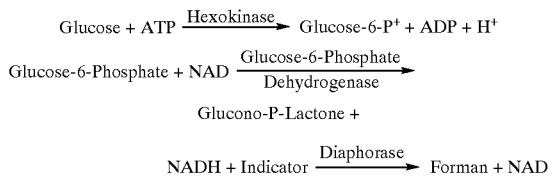

In accordance with that embodiment, a device of the present invention comprises a detection matrix that contains the substrates, enzymes and indicators needed for the hexokinase detection of glucose. Those reagents comprise adenosine triphosphate (ATP), nicotinamide adenine dinucleotide (NAD), hexokinase, glucose-6-phosphate dehydrogenase, diaphorase and an indicator. A preferred indicator is a tetrazolium salt such as 2-(p-Iodophenyl)-3-(p-nitrophenyl)-5-phenyltetrazolium chloride (i.e., INT), p-Nitro Blue Tetrazolium chloride (i.e., NBT) or 2-(4-difluoromethyl-5-chlorothiazolyl)-3-(3,4,5-trimethoxyphenyl)-5-(3,4-methylenedioxyphenyl) tetrazolium benzensulfonate.

In another preferred embodiment, an analyte is cholesterol. Where the analyte is cholesterol, preferred chemical reagents in a detection matrix include a tetrazolium salt such as 2-(p-Iodophenyl)-3-(p-nitrophenyl)-5-phenyltetrazolium chloride (i.e., INT), p-Nitro Blue Tetrazolium chloride (i.e., NBT) or 2-(4-difluoromethyl-5-chlorothiazolyl)-3-(3,4,5-trimethoxyphenyl)-5-(3,4-methylenedioxyphenyl) tetrazolium benzensulfonate, diaphorase, cholesterol esterase and cholesterol dehydrogenase.

Where an analyte is triglyceride, preferred chemical reagents in a detection matrix include a tetrazolium indicator, magnesium sulfate, ATP, NAD, Lipase, glycerol-3-phosphate dehydrogenase and Diaphorase.

Where an analyte is amylase, preferred chemical reagents in a detection matrix include p-nitro-malthoheptoside, glucoamylase, alpha-glucosidase and calcium chloride.

A detection matrix can further comprise a buffer to maintain pH and inactive ingredients for stability. A preferred buffer is HEPES or Pipes.

A device of the present invention comprises a separation matrix vertically adjacent to a detection means and substantially aligned coincident to that detection means such that an analyte can move from the separation matrix to the detection means. The separation matrix is in contact with the detection means and compressed together 14 to 43 percent based on a relaxed state.

In a preferred embodiment, a separation matrix is a membrane filter fabricated of natural or synthetic chemically-resistant and chemically-inert materials. In an especially preferred embodiment, a separation matrix is a glass fiber filter. Preferably a separation matrix is highly porous to allow for movement of an analyte across the membrane filter and into a detection means. Porous glass fiber filters are commercially available (e.g., Whatman, Ltd., England).

Where aligned vertically adjacent to a detection means in a device of the present invention, a separation matrix can be seen to have a sample application side adjacent to a cover portion and a reagent side adjacent to a detection means. In a preferred embodiment, a separation matrix is heterogeneous with respect to those sides.

In a preferred embodiment, those sides are heterogeneous with respect to the lateral spreading of a liquid sample applied to the matrix. According to this embodiment, the application side of a separation matrix promotes lateral spreading of an applied liquid sample to a lessor extent than the reagent side. Thus, spreading of an applied sample occurs as that sample passes through a separation matrix and toward a detection means.

Where a separation matrix is a glass fiber filter, such a heterogeneous promotion of lateral spreading is accomplished by having the glass fibers at the reagent side shorter than the glass fibers at the application side. The use of such a heterogeneous glass fiber filter reduces the amount of sample needed for detection of an analyte in that sample and reduces the time need for such detection.

A separation matrix can further contain a substance that interacts with an applied sample so long as that substance does not adversely affect detection of an analyte. An exemplary such substance is an agent that promotes aggregation of colloidal particles or cells and serve to enhance separation of an analyte from other substances that likely interfere with analyte detection.

By way of example, where a liquid sample is blood, and means for detecting an analyte is a colorimetric means, the presence of red blood cells would likely interfere with color detection. Red blood cells can be aggregated in a separation matrix such that those cells do not migrate to a detection matrix and interfere with color detection. A preferred aggregation-promoting substance for use with whole blood samples is an agglutination-promoting agent such as a lectin. A preferred lectin is potato lectin.

A separation matrix can also comprise a surface active agent such as a surfactant. Where a sample is whole blood, a preferred surfactant is a non-hemolytic surfactant such as a functionalized derivative of polyoxethylene (e.g., Cremophor EL, Sigma Chem. Co., St. Louis, Mo.) or Surfynol 465 (Air Products and Chemicals, Inc.).

A separation matrix can also comprise a buffer that regulates pH within a predetermined range. Where an analyte is glucose and a detection means is the hexokinase reaction, pH is preferably from about a value of 7.0 to about a value of 8.0 and, preferably about a value of 7.5. A preferred buffer for use in detection of glucose using the hexokinase detection means is 4-(2-hydroxyethyl)-1-piperazine-ethanesulfonic acid (HEPES).

The cross-sectional area of an aperture in the cover portion is less than about ninety percent of the cross-sectional area of the separation matrix and, preferably, is less than about fifty percent of the cross-sectional area of the separation matrix.

In a preferred embodiment, a liquid sample is a sample of extracellular fluid as exemplified by whole blood.

II. Glucose Assay Device

A preferred analyte that is detected by a device of the present invention is glucose. Such a device is particularly suited for detecting glucose in a liquid biological sample and, more preferably in blood.

Thus, in accordance with such a more preferred embodiment, the present invention contemplates a device for assaying blood glucose, which in a preferred form comprises:

a) a plastic base portion having a polycarbonate clear window;

b) a means for detecting glucose vertically adjacent to the base portion and at least partially coincident with the window, which detection means comprises ATP, NAD, hexokinase, glucose-6-phosphate dehydrogenase, diaphorase and an indicator;

c) a separation matrix vertically adjacent to, compressed to and substantially coincident with that reagent membrane; and d) a thermoformed polystyrene cover portion having an aperture, the cross-sectional area of which aperture is less than 90 percent of the cross-sectional area of the separation matrix.

Preferably, a separation matrix used in such a glucose detection device is a glass fiber filter. Such a filter preferably contains HEPES and can further contain a red blood cell aggregation-promoting substance such as potato lectin and a non-hemolytic surfactant such as Cremophor EL.

In a preferred embodiment, a separation matrix in such a device is heterogeneous with respect to the lateral spreading of a liquid sample applied to the filter. Where a separation matrix is a glass fiber filter, the application side of the filter promotes lateral spreading of an applied liquid sample to a lessor extent than the reagent side. Preferably, the glass fibers at the reagent side shorter than the glass fibers at the application side of a glass fiber filter. The use of such a heterogeneous glass fiber filter reduces the amount of sample needed for detection of an analyte in that sample and reduces the time need for such detection.

III. A Process of Detecting an Analyte in a Biological Fluid

In another aspect, the present invention contemplates a process for detecting an analyte in a biological fluid. In accordance with such a process, a sample of biological fluid is applied through an aperture to a separation matrix of a detection device comprising:

a) a base portion having a transparent window:

b) a means for detecting the analyte vertically adjacent to the base portion and at least partially coincident with the window;

c) a separation matrix vertically adjacent to, compress to and substantially coincident with the detection means; and d) a cover portion having an aperture, the cross-sectional area of which aperture is less than 90 percent of the cross-sectional area of the separation matrix.

The device with the applied sample is then maintained at a temperature and for a period of time sufficient for the analyte in the sample to traverse the separation matrix, enter the detection means, interact with the detecting means and generate a detectable signal indicative of analyte presence or proportional to the amount or concentration of glucose present. The generated signal is then detected visually through the transparent window in the base portion.

The device with the sample applied thereto is preferably maintained at a temperature of from about 4° C. to about 50° C., more preferably from about 15° C. to about 30° C. and, even more preferably at about 25° C.

In a preferred embodiment, maintenance time is less than about two minutes, and more preferably less than about one minute. Preferably, the sample is applied to the device in a volume of from about 5 microliter ($\mu$l) to about 20 $\mu$l, more preferably from about 5 $\mu$l to about 15 $\mu$l and, even more preferably from about 3 $\mu$l to about 10 $\mu$l.

A separation matrix and means for detecting an analyte are preferably the same as set forth above. The cross-sectional area of the aperture in the cover portion is less than about ninety percent of the cross-sectional area of the separation matrix and, more preferably, less than about fifty percent of the cross-sectional area of the separation matrix. The separation matrix and detection means are under a compression of 14 to 43 percent and, preferably, 20 to 35 percent, based on an uncompressed (relaxed) state.

The following Examples illustrate particular embodiments of the present invention and are not limiting of the claims and specification in any way.

EXAMPLE 1

Construction of Analyte Detection Device

Multiple layers of thin plastic sheets and adhesive tape were used to construct the detection device. The overall thickness of the device can be varied by using varying numbers of layers. Such various layers can be adhered to each other using a suitable adhesive. An exemplary and preferred adhesive is double-sided adhesive tape purchased from 3M. The layers of the device were constructed of high density polystyrene sheets (0.006" thick) purchased from American Can.

After adhering a desired number of plastic sheets together, holes were punched through the adhered layers to make a cavity for the separation and detection layers. A clear bottom layer was added, the detection and separation layers inserted and a top layer with application site was added to enclose the layers within the device. Either polyester, polycarbonate or polyethylene terephthalate was used for the top and bottom layers. A schematic diagram of a detection device of the present invention is shown in FIG. 1.

EXAMPLE 2

Effects of Aperture Size

A glass fiber filter [Whatman, Ltd.(PD107)] was impregnated with a solution containing 1.3 percent (w/w) Cremophor EL (Sigma Chem. Co.). The impregnated glass filter was dried in the hot air oven at about 50° C. for 15 minutes.

A synthetic membrane fabricated of nylon (Biodyne A, 0.45 micron pore size, PALL Biosupport, Long, Island, N.Y.) was cut impregnated with ATP, NAD, hexokinase, glucose-6-phosphate (G-6-P) dehydrogenase, diaphorase and NBT (a tetrazolium salt, Sigma Chem. Co.). Impregnation was accomplished by soaking the synthetic membrane in an appropriate aqueous solution having, for example, the following final concentrations:

5.5% (w/w) Tetrazolium indicator (e.g. NBT)

1% (w/w) NAD 4.7% (w/w) ATP 0.7% (w/w) Magnesium Acetate 0.4% (w/w) Bovine Serum Albumin 800 U/mL Hexokinase 800 U/mL Glucose-6-phosphate Dehydrogenase 800 U/mL Diaphorase 3.7% (w/w) HEPES buffer at pH 7.5

2% inactive ingredients

The chemicals were obtained from Sigma Chem. Co. The detection matrix was incorporated with chromogenic indicator first. It was dried in a hot air oven at 50° C. for 5 minutes. The dried matrix was then impregnated with the aqueous solution containing the buffer, substrates/cofactors and enzymes. The impregnated matrix was dried again at 50C for 10 minutes.

Separation matrix disks and detection disks of 0.185 inch and 0.25 inch were employed. The glass fiber filter and impregnated synthetic membrane (detection matrix) were sandwiched between a plastic base portion having a transparent polycarbonate window and a polystyrene cover having an aperture of 0.07, 0.10, 0.15 or 0.18 inches in accordance with the procedures set forth in Example 1. The filter and membrane were compressed 30 percent based from their relaxed state.

From about 3 µl to about 16 µl of whole blood were applied to the glass fiber filter through the aperture in the polystyrene cover and glucose was detected using a change in color.

Data from these studies is summarized in FIG. 2. The data show a direct correlation between minimum sample volume and aperture size. The data also show that where the diameter of the glass fiber filter is 0.19 inches, and the aperture diameter is 0.07 inches, as little as 5 µl of blood is need to generate a detectable signal.

EXAMPLE 3

Other Analytes

A detection device for other analytes can be prepared using the procedures set forth above. The following impregnation solutions are exemplary of solutions that can be used to impregnate detection matrices for use with the detection of cholesterol, triglyceride and amylase.

Cholesterol:
1.5% (w/w) tetramethylbenzidine hydrochloride indicator dye
4% (w/w) Pipes buffer at pH 7.0
240 U/mL Peroxidase
240 U/mL Cholesterol Esterase
120 U/mL Cholesterol Oxidase
12% inactive ingredients Triglyceride:
1.1% (w/w) Tetrazolium indicator
2.4% (w/w) HEPES buffer at pH 7.5
0.7% (w/w) Magnesium sulfate
2.7% (w/w) ATP
7.1% (w/w) NAD
25000 U/mL Lipase
800 U/mL Lipase
1000 U/mL Glycerol-3-Phosphate Dehydrogenase
500 U/mL Diaphorase
1.5% inactive ingredients Amylase:
17.3% (w/w) p-nitro-maltoheptoside (Genzyme Co.)
16 U/mL Glucoamylase
70 U/mL Alpha-Glucosidase
1.7% (w/w) Pipes, pH 7.0
5 mM Calcium Chloride While the compositions and methods of this invention have been described in terms of preferred embodiments, it will be apparent to those of skill in the art that variations can be applied to the composition, process and in the steps or in the sequence of steps of the process described herein without departing from the concept, spirit and scope of the invention.

What is claimed is:

1. A device for rapidly detecting an analyte in a volume of biological fluid, wherein the volume is as low as five to ten microliters, said device comprising:
   a) means for detecting said analyte; and
   b) a separation matrix vertically adjacent, compressed to and coincident with said detection means such that analyte applied to said separation means can move from said separation matrix to said detection means, wherein said separation matrix and said detection means are under a volume compression of between 14 to 43 percent;
   c) a cover portion having an aperture, the cross-sectional area of which aperture is less than 90 percent of the cross-sectional area of said separation matrix; and
   d) a base portion containing an access means to allow detection of an analytical signal generated by the detection means.

2. The device according to claim 1 wherein said detection means is a detection matrix containing one or more chemical reagents that interact with said analyte to generate a detectable signal indicative of the presence or amount of analyte.

3. The device according to claim 2 wherein said detection matrix is a membrane.

4. The device according to claim 1 wherein said separation matrix is a membrane filter.

5. The device according to claim 4 wherein said membrane filter is a glass fiber filter.

6. The device according to claim 5 wherein said glass fiber filter has a sample application side directed away from said detection means and a reagent side directed toward and adjacent to said detection means, whereby said reagent side has shorter fibers than said application side.

7. The device according to claim 1 wherein said separation matrix contains an aggregation-promoting substance that promotes aggregation of colloidal particles or cells.

8. The device according to claim 1 wherein said separation matrix contains a surface active agent.

9. The device according to claim 8 wherein said surface acting agent is a non-hemolytic surfactant.

10. The device according to claim 1 wherein the cross-sectional area of the aperture is less than 50 percent of the cross-sectional area of said separation matrix.

11. The device according to claim 1 wherein said separation matrix and said detection means are under compression of between 20 and 35 percent.

12. The device according to claim 1 wherein said biological fluid is whole blood.

13. The device according to claim 1 wherein said analyte is selected from the group consisting of glucose, cholesterol and triglyceride.

14. The device according to claim 13 wherein the analyte is glucose and said detection means comprises a membrane containing ATP, NAD, hexokinase, glucose-6-phosphate dehydrogenase, diaphorase and an indicator.

15. The device according to claim 14 wherein said separation matrix contains HEPES.

16. A process of rapidly detecting glucose in a volume of a biological fluid, wherein said volume is as low as five to 10 microliters, said process comprising the steps of:
   a) a base portion having a transparent window;
   b) a means for detecting glucose vertically adjacent to said base portion and at least partially coincident with said window;
   c) a separation matrix vertically adjacent to, compressed to and substantially coincident with said detection means, wherein the detection means and the separation matrix are under a volume compression of between 14 10 43 percent; and
   d) a cover portion having an aperture, the cross-sectional area of which aperture is less than 90 percent of the said separation matrix.

17. The device according to claim 16 wherein said separation matrix contains HEPES.

18. The device according to claim 16 wherein said detection means comprises a membrane containing ATP, NAD, hexokinase, glucose-6-phosphate dehydrogenase, diaphorase and an indicator.

19. A process of rapidly detecting an analyte in a biological fluid, said process comprising the steps of:
  a) providing a detection device comprising:
    i) means for detecting said analyte;
    ii) a separation matrix vertically adjacent to, compressed to and coincident with said detection means such that said analyte can move from said separation matrix to said detection means, wherein said detection means and said separation matrix are under a volume compression of 14 to 43 percent;
    iii) a cover portion having an aperture, the cross-sectional area of which is less than 90 percent of the cross-sectional area of the said separation matrix; and
    iv) a base portion containing an access means to allow detection of an analytical signal generated by the detection means;
  b) applying a volume of a sample of said biological fluid, wherein the volume is as low as five to ten microliters, to said separation matrix;
  c) maintaining said detection device at a temperature and for a period of time sufficient for said analyte to traverse said separation matrix, enter said detection means and interact with said means to generate a detectable signal indicative of the presence or amount of said analyte; and
  d) detecting said signal.

20. The process according to claim 19 wherein said biological fluid is extracellular fluid.

21. The process according to claim 20 wherein said extracellular fluid is whole blood.

22. The process according to claim 19 wherein said separation matrix is a membrane filter.

23. The process according to claim 22 wherein said membrane filter is a glass fiber filter.

24. The process according to claim 23 wherein said glass fiber filter has a sample application side directed away from said detection means and a reagent side directed toward and adjacent to said detection means, whereby said reagent side has shorter fibers than said application side.

25. The process according to claim 19 wherein said separation matrix contains an aggregation-promoting substance that promotes aggregation of colloidal particles or cells.

26. The process according to claim 19 wherein said separation matrix contains a surface active agent.

27. The process according to claim 26 wherein said surface acting agent is a non-hemolytic surfactant.

28. The process according to claim 19 wherein said separation matrix contains a buffer.

29. The device according to claim 1 wherein said access means in the base portion is an aperture.

30. The device according to claim 29 wherein the aperture contains a transparent window.

31. The process according to claim 19 wherein said access means in the base portion of the device is an aperture.

32. The process according to claim 31 wherein the aperture contains a transparent window.

* * * * *